United States Patent
Karasawa et al.

(10) Patent No.: US 8,088,065 B2
(45) Date of Patent: Jan. 3, 2012

(54) MEDICAL INSTRUMENT

(75) Inventors: Hitoshi Karasawa, Hachioji (JP); Daisuke Asada, Hachioji (JP); Sho Nakajima, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 12/727,571

(22) Filed: Mar. 19, 2010

(65) Prior Publication Data

US 2010/0249502 A1 Sep. 30, 2010

Related U.S. Application Data

(63) Continuation of application No. PCT/JP2009/066297, filed on Sep. 17, 2009.

(30) Foreign Application Priority Data

Oct. 29, 2008 (JP) .................................. 2008-278630

(51) Int. Cl.
*A61B 1/12* (2006.01)

(52) U.S. Cl. ........ 600/157; 600/121; 600/122; 600/173; 600/176; 600/177

(58) Field of Classification Search .......... 600/121–125, 600/137, 157, 173, 176–177
See application file for complete search history.

(56) References Cited

U.S. PATENT DOCUMENTS

| | | | | |
|---|---|---|---|---|
| 5,392,766 A | * | 2/1995 | Masterson et al. | 600/157 |
| 5,518,502 A | * | 5/1996 | Kaplan et al. | 600/157 |
| 6,258,025 B1 | * | 7/2001 | Swallert | 600/157 |
| 6,371,909 B1 | * | 4/2002 | Hoeg et al. | 600/173 |
| 6,537,209 B1 | * | 3/2003 | Pinkhasik et al. | 600/170 |
| 6,755,782 B2 | * | 6/2004 | Ogawa | 600/127 |
| 6,923,759 B2 | * | 8/2005 | Kasahara et al. | 600/157 |
| 7,316,683 B2 | * | 1/2008 | Kasahara et al. | 606/45 |
| 7,625,338 B2 | * | 12/2009 | Gilad et al. | 600/173 |
| 7,959,561 B2 | * | 6/2011 | Akui et al. | 600/157 |
| 2008/0081948 A1 | * | 4/2008 | Weisenburgh et al. | 600/121 |

* cited by examiner

*Primary Examiner* — Matthew J Kasztejna
(74) *Attorney, Agent, or Firm* — Scully, Scott, Murphy & Presser, P.C.

(57) ABSTRACT

A medical instrument includes an image pickup section incorporated in a medical instrument body and movably provided in the medical instrument body that picks up an image of the object to be examined from an observation window, a covering section movably provided at the medical instrument body so as to cover the observation window and in which an opening portion is formed, a drive section that drives the covering section or the image pickup section, and a control section that controls the drive section so as to drive the covering section or the image pickup section by synchronizing a timing for the image pickup section to pick up the object image with a timing at which the opening portion and the observation window match, and can thereby prevent sticking of deposits to the observation window and obtain a clear observation image.

8 Claims, 9 Drawing Sheets

MEDICAL INSTRUMENT

CROSS REFERENCE TO RELATED APPLICATION

This application is a continuation application of PCT/JP2009/066297 filed on Sep. 17, 2009 and claims benefit of Japanese Application No. 2008-278630 filed in Japan on Oct. 29, 2008, the entire contents of which are incorporated herein by this reference.

BACKGROUND OF THE INVENTION

1. Field of the Invention

The present invention relates to a medical instrument provided with image pickup means for observing inside of a patient's body.

2. Description of the Related Art

As is well known, endoscope apparatuses, which are medical instruments, are provided with an image pickup apparatus, which is image pickup means, designed to be introduced into a body cavity of a patient and perform various types of inspections and treatments of affected areas in the body based on observed images taken by the image pickup apparatus. Examples of such endoscopes include those introduced into digestive organs such as esophagus, stomach, large intestine and duodenum, which are tube cavities and tubes in the body, from the oral cavity or anus and those introduced into the abdominal cavity from the vicinity of the umbilical region by puncturing through the body wall.

Endoscope apparatuses for medical care are used in such an environment that contamination such as mucous membranes, waste or blood in the body is stuck to the observation window of the image pickup apparatus or vapor is stuck to the observation window of the image pickup apparatus in a humid environment in the body causing fogging of the observation window, and these deposits may thereby impair visibility, preventing clear images from being taken. Thus, conventionally, various proposals to remove deposits stuck to the observation window of image pickup apparatuses have been presented.

For example, Japanese Patent Application Laid-Open Publication No. 8-29699 discloses an image scope provided with a wiper for wiping contamination on the outer surface of an objective lens. Furthermore, for example, Japanese Patent Application Laid-Open Publication No. 5-103748 discloses a catheter apparatus for an endoscope provided with a catheter body into which an endoscope is inserted whose observation window and channel opening portion are exposed at a distal end portion.

Techniques of conventional catheter apparatuses for an endoscope are disclosed which form a shielding member that shields at least part of an opening portion or the like of a channel at a distal end portion of the endoscope at the distal end portion of the catheter body and are also provided with a lock mechanism as suppressing means for suppressing relative rotation between the endoscope and the catheter body and capable of opening/closing the channel opening portion as required. Furthermore, a wiping member such as a buff is provided on the back of the shielding member and the wiping member is configured to be able to remove contamination or the like stuck to the observation window and illumination window of the endoscope.

SUMMARY OF THE INVENTION

A medical instrument of the present invention that observes an interior of an object to be examined, including an image pickup section incorporated in a medical instrument body and movably provided in the medical instrument body that picks up an image of the object to be examined from an observation window, a covering section movably provided at the medical instrument body so as to cover the observation window and in which an opening portion is formed, a drive section that drives the covering section or the image pickup section, and a control section that controls the drive section so as to drive the covering section or the image pickup section by synchronizing a timing for the image pickup section to pick up the object image with a timing at which the opening portion and the observation window match.

DETAILED DESCRIPTION OF THE PREFERRED EMBODIMENT(S)

Hereinafter, embodiments of the present invention will be described with reference to the accompanying drawings. In the following descriptions, a medical instrument provided with image pickup means used for a laparoscopic surgical operation will be taken as an example.

First Embodiment

Figure 1:
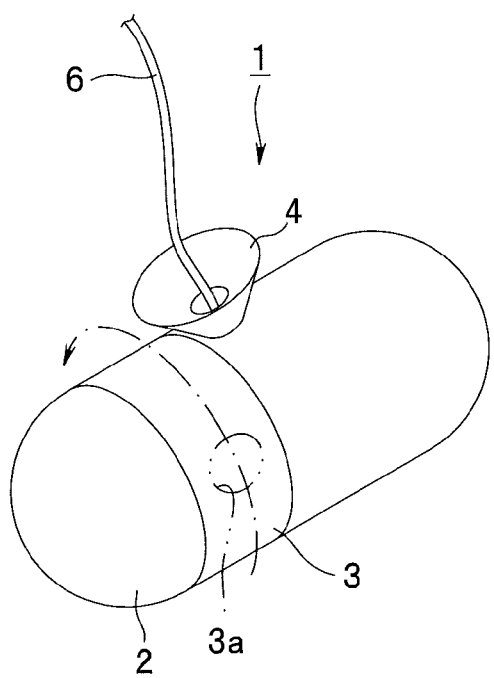
FIG. 1 is a perspective view illustrating a configuration of a camera set up in the abdominal cavity according to a first embodiment.
Figure 2:
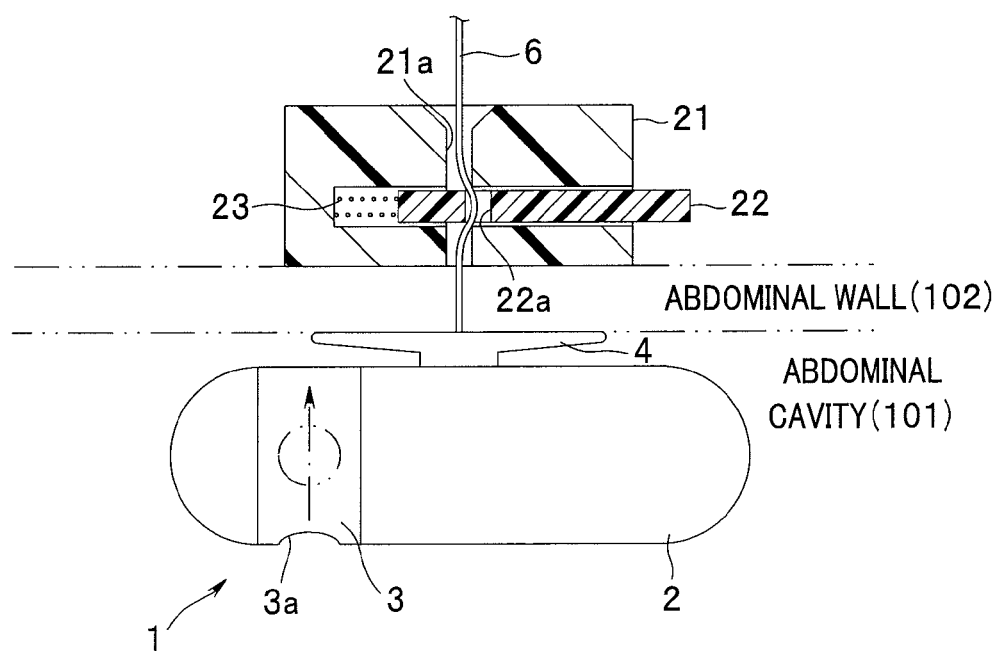
FIG. 2 is a partial cross-sectional view illustrating the camera set up in the abdominal cavity according to the first embodiment, which is set up in the abdominal cavity.
Figure 3:
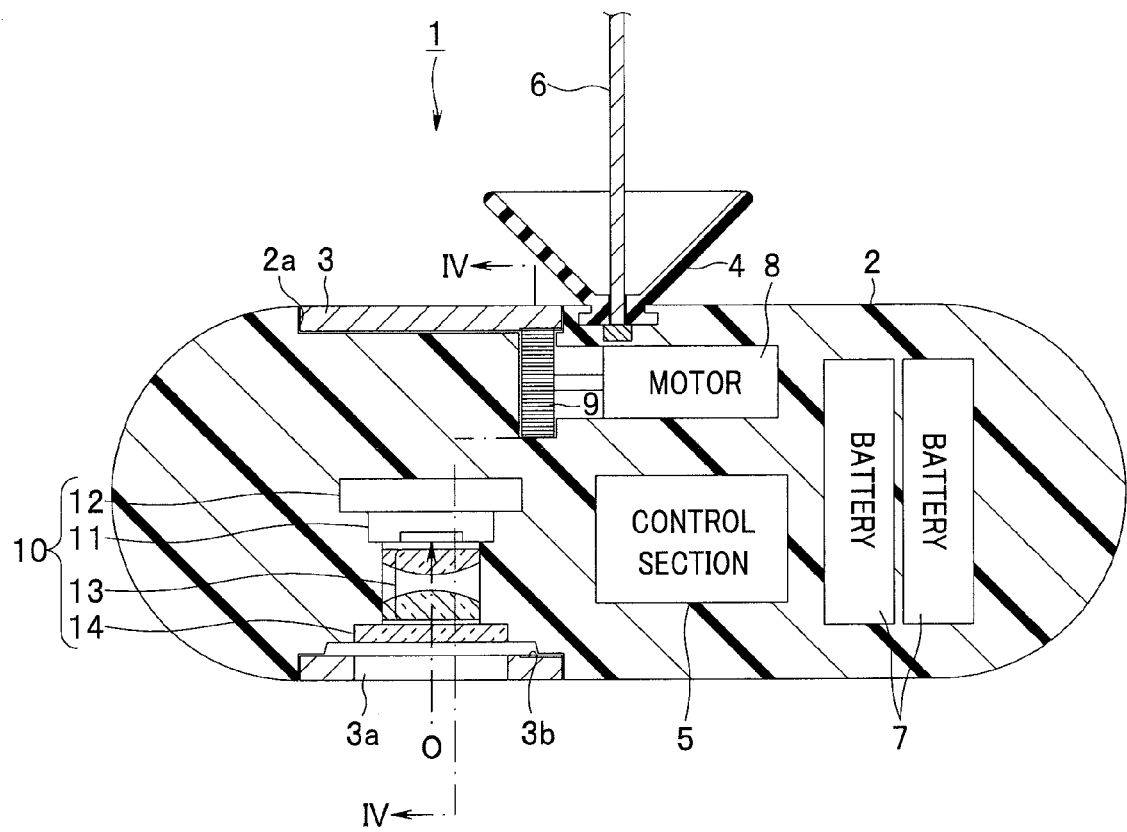
FIG. 3 is a cross-sectional view illustrating a configuration of the camera set up in the abdominal cavity according to the first embodiment.
Figure 4:
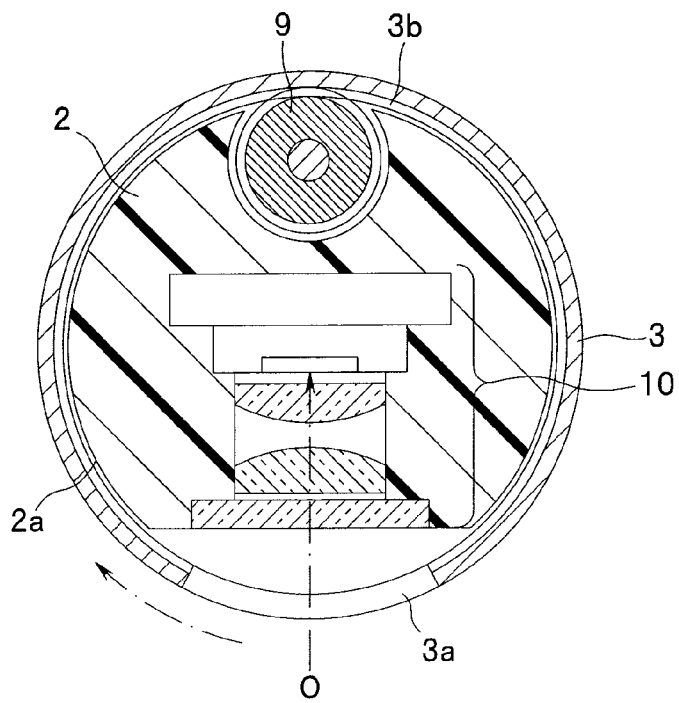
FIG. 4 is a cross-sectional view along a line IV-IV in FIG. 3 illustrating the configuration of the camera set up in the abdominal cavity according to the first embodiment.
Figure 5:
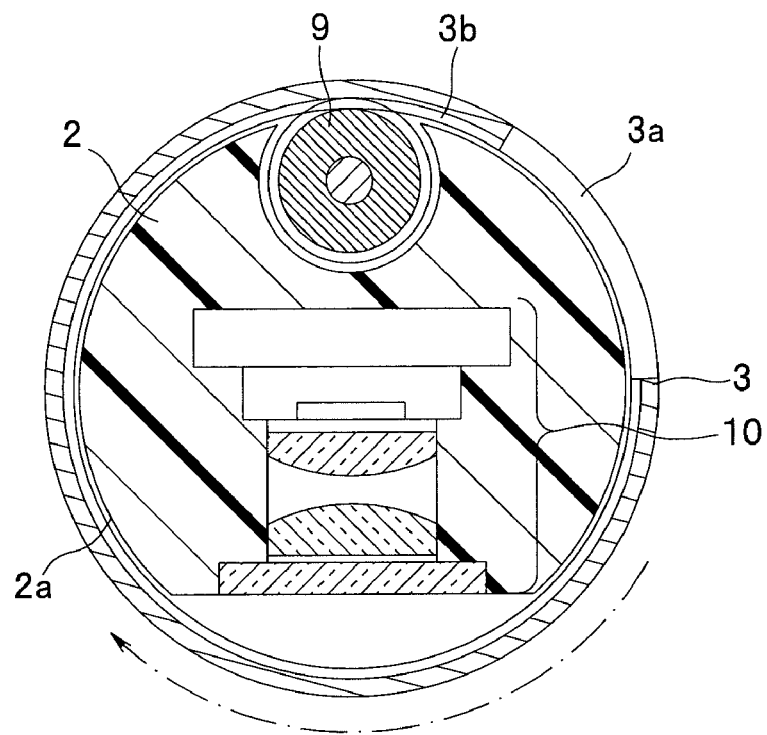
FIG. 5 is a cross-sectional view illustrating the camera set up in the abdominal cavity according to the first embodiment when a rotating cover rotates around the outer perimeter of a camera body.
Figure 6:
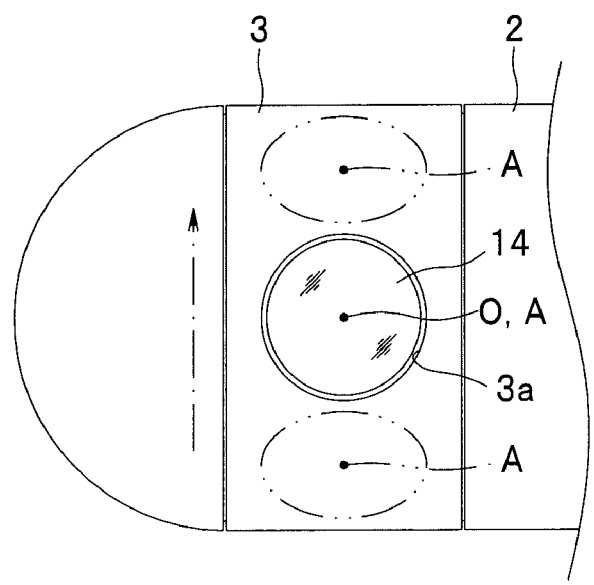
FIG. 6 is a plan view illustrating the camera set up in the abdominal cavity according to the first embodiment when the rotating cover rotates around the outer perimeter of the camera body.

First, a camera set up in the abdominal cavity, which is a medical instrument according to the present invention used for a laparoscopic surgical operation will be described below. FIG. 1 to FIG. 6 are related to the first embodiment of the present invention, FIG. 1 is a perspective view illustrating a configuration of the camera set up in the abdominal cavity, FIG. 2 is a partial cross-sectional view illustrating the camera set up in the abdominal cavity, which is set up in the abdominal cavity, FIG. 3 is a cross-sectional view illustrating the configuration of the camera set up in the abdominal cavity, FIG. 4 is a cross-sectional view along a line IV-IV in FIG. 3 illustrating the configuration of the camera set up in the abdominal cavity, FIG. 5 is a cross-sectional view illustrating the camera set up in the abdominal cavity when a rotating cover rotates around the outer perimeter of a camera body and FIG. 6 is a plan view illustrating the camera set up in the abdominal cavity when the rotating cover rotates around the outer perimeter of the camera body.

As shown in FIG. 1 to FIG. 4, the camera set up in the abdominal cavity (hereinafter simply referred to as "camera") 1, which is a medical instrument of the present embodiment is mainly configured by including a camera body 2, which is the medical instrument body having a capsule-shaped appearance with built-in image pickup means (image pickup section), a rotating cover 3, which is covering means (covering section) rotatably disposed around the outer perimeter of the camera body 2, a suction cup 4, which is fixing means fitted into the camera body 2 constituting an abdominal wall fixing section, and a wire 6 that extends from the center of the suction cup 4. The camera 1 is provided with an illumination unit (not shown) that irradiates illumination light onto an object.

The camera 1 of the present embodiment is used for a laparoscopic surgical operation and used to take images of a treatment region when treating an organ or the like in the abdominal cavity 101, which is one of a patient's body cavities.

First, the camera 1 is introduced into the patient's abdominal cavity 101 via a trocar (not shown) punctured through the abdominal wall 102. The wire 6 is hooked onto the camera 1 by a puncture needle or the like (not shown) punctured into the abdominal cavity 101 and pulled out of the body by passing through the abdominal wall 102.

Next, the wire 6 of the camera 1 is passed through a hole portion 21a of a fixing unit 21 prepared on the abdomen side of the patient and pulled toward the abdominal wall 102 side. The camera 1 is then lifted so that the camera 1 comes closer to the abdominal wall 102 and pulled toward the outside of the body until the suction cup 4 sticks fast to the inner surface of the abdominal wall 102. Thus, when the suction cup 4 sticks fast to the abdominal wall 102, the camera 1 is left indwelling and fixed in the abdominal cavity 101.

The fixing unit 21 is provided with a fixing lever 22 that fixes the wire 6 of the camera 1 outside the body. A hole portion 22a through which the wire 6 passes is formed at some midpoint of the fixing lever 22 and the fixing lever 22 is urged in one sideward direction of the fixing unit 21 by a spring 23 provided in the fixing unit 21 so that the position of the hole portion 22a is deviated from the position of the hole portion 21a of the fixing unit 21.

That is, when the user pushes the fixing lever 22 into the fixing unit 21 up to a position at which the hole portion 21a of the fixing unit 21 substantially matches the hole portion 22a of the fixing lever 22 against the urging force of the spring 23, the user can easily pull the wire 6. When the user stops pushing the fixing lever 22 into the fixing unit 21, the fixing lever 22 then slides by receiving the urging force of the spring 23.

Therefore, since the position of the hole portion 22a of the fixing lever 22 deviates from the position of the hole portion 21a of the fixing unit 21, the wire 6 of the camera 1 that passes through the hole portions 21a and 22a is sandwiched and fixed in the fixing unit 21. Thus, the camera 1 is left indwelling and fixed in the abdominal cavity 101 in a stable state in which the suction cup 4, which is the abdominal wall fixing section, sticks fast to the abdominal wall 102.

Next, as described above, a more specific configuration of the camera 1 left indwelling and fixed in the body, the abdominal cavity 101 here, will be described in detail using FIG. 3 and FIG. 4.

The camera body 2 of the camera 1 incorporates a control section 5, which is control means constituting a controller, (here two) batteries 7 constituting a power supply section, a motor 8 which is drive means (drive source) constituting a drive section, and an image pickup unit 10 constituting an image pickup section, which is image pickup means here.

The control section 5 is provided with a transmitter that transmits an image signal photoelectrically converted by the image pickup unit 10 to an external device and a receiver (neither is shown) that receives a drive instruction signal of the motor 8 transmitted from the external device and drives/controls the motor 8 according to the received drive instruction signal.

Furthermore, the two batteries 7 constitute a power supply section to drive the control section 5, the motor 8, the image pickup unit 10 and the illumination unit (not shown). The two batteries 7 are electrically connected to the control section 5 via a power supply electric cable (not shown) and the control section 5 is provided with wiring of communication cables (not shown) for power supply and exchange of signals individually connected to the motor 8, the image pickup unit 10 or the like.

Furthermore, the image pickup unit 10 is configured by including a solid image pickup device 11 such as CCD, CMOS, an image pickup substrate 12 on which the solid image pickup device 11 is mounted, a plurality of objective lenses 13 and a cover lens 14 serving as an observation window. The image pickup unit 10 outputs a photoelectrically converted image signal to the control section 5. The control section 5 transmits the image signal from an internal transmitter to a camera control unit (CCU) which is an external device (not shown). The image taken by the image pickup unit 10 is subjected to image processing by the CCU and displayed on an outside monitor (not shown).

A peripheral groove 2a is formed in the outer perimeter of the camera body 2, on which the aforementioned rotating cover 3 is rotatably disposed. In the peripheral groove 2a, the cover lens 14 of the image pickup unit 10 is disposed so as to be exposed from the bottom of the camera body 2.

Thus, the rotating cover 3 disposed in the peripheral groove 2a of the camera body 2 has a cylindrical shape and a circular opening portion 3a is formed which has substantially the same shape as the cover lens 14 of the image pickup unit 10.

Furthermore, a gear groove 3b is formed which is meshed with a spur gear 9 of the motor 8 incorporated in the camera body 2 in the inner perimeter on one side of the rotating cover 3.

That is, the rotating cover 3 rotates around the outer perimeter on the peripheral groove 2a of the camera body 2 by a rotation force of the gear 9 transmitted through driving of the motor 8.

The camera 1 of the present embodiment configured as described above is introduced into the abdominal cavity 101 as shown in FIG. 2 and when the camera 1 is used by being left indwelling and fixed in the abdominal wall 102, if the gear 9 is rotated by being driven by the motor 8 through a wireless operation from outside, the rotating cover 3, which is meshed with the gear 9, rotates around the outer perimeter of the camera body 2.

In this case, the opening portion 3a formed in the rotating cover 3 moves along the outer perimeter of the camera body 2 as shown in FIG. 5 and FIG. 6. Furthermore, the rotating cover 3 moves around the outer perimeter of the camera body 2 so that a center position A, which is the center of the opening of the opening portion 3a, passes through a position at which the center position A matches an optical axis O of the object image taken by the image pickup unit 10.

Thus, in the camera 1 left indwelling in the body (abdominal cavity 101), the rotating cover 3 is controlled so as to always rotate around the outer perimeter of the camera body 2 when an image of an object to be examined such as an organ in the body (abdominal cavity 101) is taken.

The control section 5 of the camera 1 controls driving of the motor 8 that causes the rotating cover 3 to rotate so that the timing at which the opening portion 3a of the rotating cover 3 moves to a position where the rotating cover 3 matches the cover lens 14 of the image pickup unit 10 is in accordance with the frame rate timing of the image pickup unit 10.

That is, when the rotating cover 3 rotates, the control section 5 controls driving of the motor 8 so that the opening portion 3a of the rotating cover 3 matches the cover lens 14 of the image pickup unit 10 in synchronization with the timing at which the image pickup unit 10 of the camera 1 picks up an object image. As described above, this timing is timing at which the center position A of the opening portion 3a of the rotating cover 3 matches the optical axis O of the object image that impinges on the image pickup unit 10.

When, for example, the frame rate of the image pickup unit 10 is 60 fps, the control section 5 performs control such that the number of revolutions that the rotating cover 3 rotates around the outer perimeter of the camera body 2 is 60 revolutions/sec so that the center position A of the opening portion 3a of the rotating cover 3 matches the optical axis O of the object image that impinges on the image pickup unit 10 in synchronization with the frame rate, that is, the timing at which the image is picked up.

As described above, the camera 1 of the present embodiment has a configuration in which the opening portion 3a of the rotating cover 3 moves to a position where it matches the cover lens 14 of the image pickup unit 10 and the cover lens 14 is exposed from the opening portion 3a of the rotating cover 3 in accordance with the moment (timing) at which the image pickup unit 10 picks up an object image. This reduces the duration that the cover lens 14 of the image pickup unit 10 of the camera 1 is exposed, and can thereby prevent blood, mucous membrane or the like from a treated diseased area from scattering over the surface of the cover lens 14 and prevent sticking of contamination such as smoke generated during treatment of the diseased area using a high frequency treatment device.

According to the above descriptions, the camera 1 of the present embodiment is configured to cause the rotating cover 3 to rotate and reduce the exposure duration of the cover lens 14 of the image pickup unit 10 that picks up an image of an object to be examined, that is, the cover lens 14 is exposed only when an object image is picked up, and therefore contamination is less likely to stick to the cover lens 14 and the image pickup unit 10 can always obtain a clear observation image.

Furthermore, the opening portion 3a of the rotating cover 3 matches the cover lens 14, which is an observation window, in accordance with the frame rate timing of the image pickup unit 10, and therefore the camera 1 never blocks the field of view and prevents any unnecessary configuration, that is, prevents the inner surface of the rotating cover 3 from being reflected during image taking.

Although a configuration has been described above where the rotating cover 3 has one opening portion 3a, the configuration is not limited thereto but a plurality of opening portions 3a may be provided in the rotating cover 3 and the control section 5 may drive/control the motor 8 so that the number of revolutions of the rotating cover 3 corresponds to the frame rate timing of the image pickup unit 10 according to the number of opening portions 3a. That is, whether the number of opening portions 3a is one or plural, any configuration may be adopted as long as the rotation of the rotating cover 3 can be controlled so that the position of the opening portion 3a matches that of the cover lens 14 according to the frame rate timing of the image pickup unit 10.

Furthermore, even when the camera 1 is not used, if the cover lens 14 of the image pickup unit 10 is moved to a position where the cover lens 14 is covered with the rotating cover 3, contamination of the cover lens 14 can be prevented.

Second Embodiment

Figure 7:
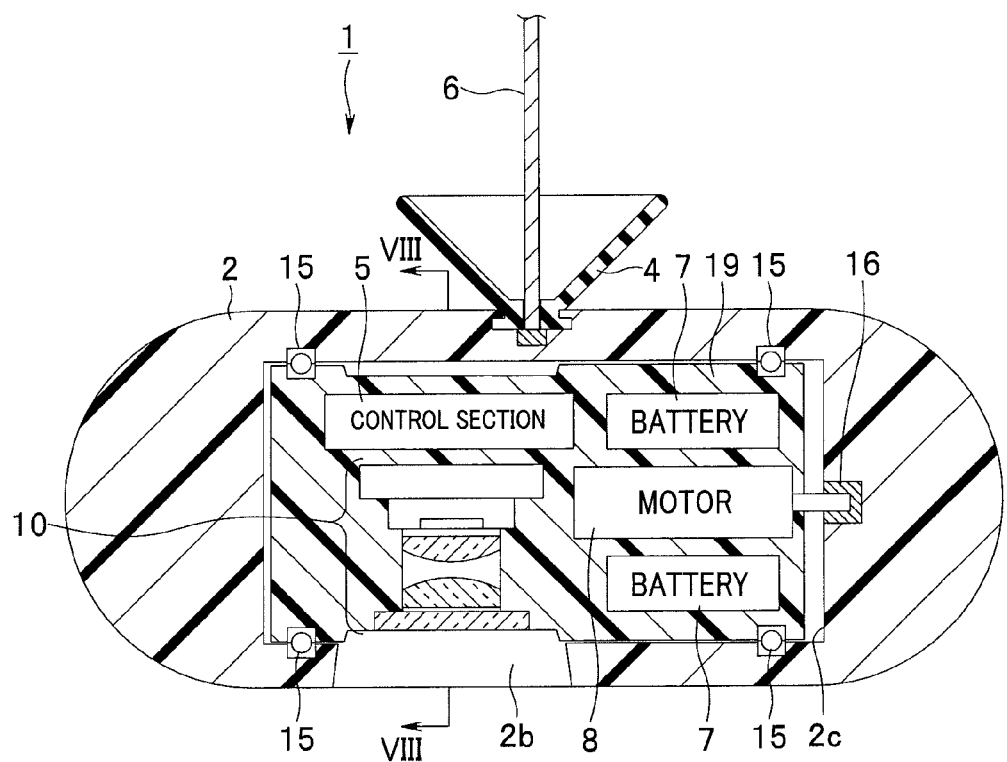
FIG. 7 is a cross-sectional view illustrating a configuration of a camera set up in the abdominal cavity according to a second embodiment of the present invention.
Figure 8:
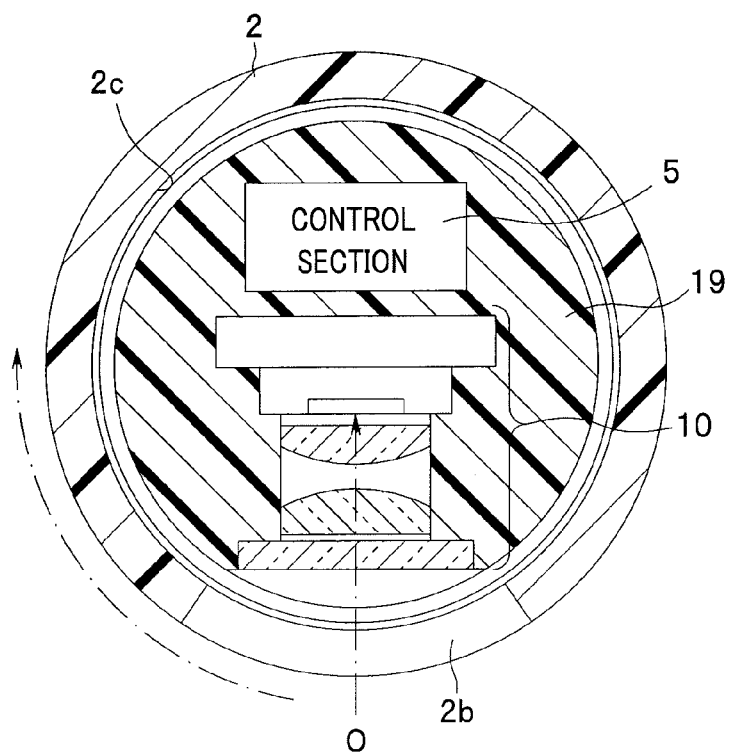
FIG. 8 is a cross-sectional view along a line VIII-VIII in FIG. 7 illustrating the configuration of the camera set up in the abdominal cavity according to the second embodiment.
Figure 9:
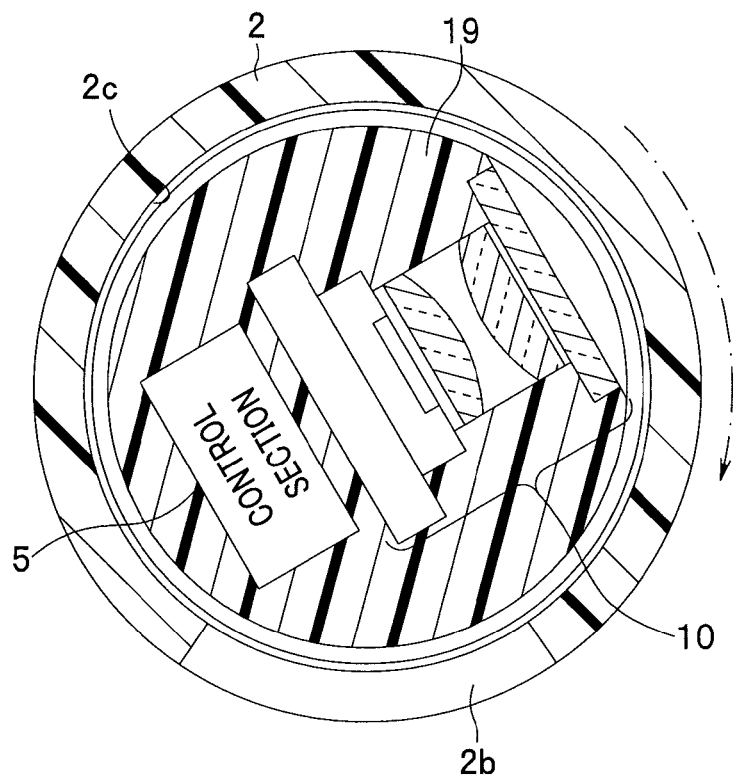
FIG. 9 is a cross-sectional view illustrating the camera set up in the abdominal cavity according to the second embodiment when a camera unit rotates in a camera body.
Figure 10:
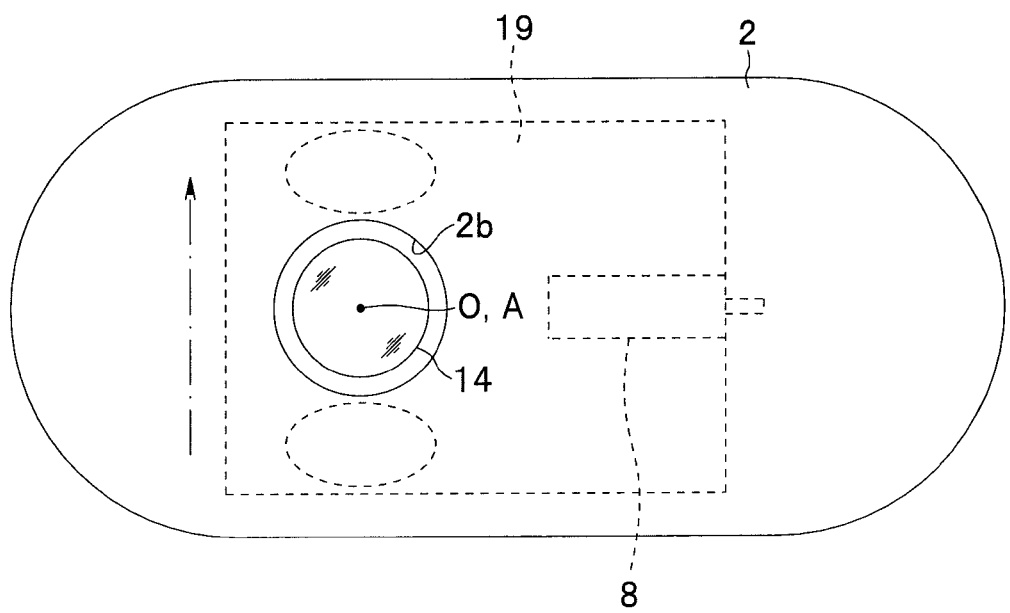
FIG. 10 is a plan view illustrating the camera set up in the abdominal cavity according to the second embodiment when the camera unit rotates in the camera body.

Next, a second embodiment of a camera set up in the abdominal cavity, which is a medical instrument according to the present invention will be described using FIG. 7 to FIG. 10 below. FIG. 7 to FIG. 10 are related to the second embodiment of the present invention, FIG. 7 is a cross-sectional view illustrating a configuration of the camera set up in the abdominal cavity, FIG. 8 is a cross-sectional view along a line VIII-VIII in FIG. 7 illustrating the configuration of the camera set up in the abdominal cavity, FIG. 9 is a cross-sectional view illustrating the camera set up in the abdominal cavity when a camera unit rotates in a camera body and FIG. 10 is a plan view illustrating the camera set up in the abdominal cavity when the camera unit rotates in the camera body. In the following descriptions, the same components as those in the camera set up in the abdominal cavity of the first embodiment will be assigned the same reference numerals and descriptions of those components and operations/effects will be omitted.

As shown in FIG. 7 and FIG. 8, the camera 1 of the present embodiment has a configuration in which a camera unit 19 rotates, which is image pickup means (image pickup section) here incorporated in the camera body 2.

To be more specific, the camera 1 is provided with an opening portion 2b in the lower part of the camera body 2 and the camera unit 19 that communicates with the opening portion 2b in the camera body 2, and a cavity 2c whose inner surface serves as covering means (covering section) is formed here. The opening portion 2b of the camera body 2 has a hole portion diameter equal to or greater than the diameter of the cover lens 14 so that the entire surface of the cover lens 14 of the image pickup unit 10 may be exposed.

The camera unit 19 incorporates the control section 5 according to the first embodiment, the two batteries 7, the motor 8 and the image pickup unit 10, and the outer perimeter on both sides is rotatably held to the camera body 2 via a bearing 15. Furthermore, in the motor 8 of the camera unit 19, a motor shaft thereof is connected and fixed to a bearing fixed to an end face that forms a cavity 2c of the camera body 2. The motor 8 is arranged in the center of the camera unit 19 so that the motor shaft protrudes from the center of one side of the camera unit 19.

Thus, the camera unit 19 is configured to rotate, driven by the motor 8 in the camera body 2. Furthermore, the opening portion 2b that communicates with the cavity 2e in which the camera unit 19 is disposed is formed on the underside of the periphery of the camera body 2 so as to allow the optical axis O of an object image taken by the image pickup unit 10 to pass when the camera unit 19 rotates around a center position A, which is the center of the opening (see FIG. 10).

The camera 1 configured as shown above is left indwelling in the body (abdominal cavity 101) as in the case of the first embodiment and is controlled so that the camera unit 19 rotates in the camera body 2 when taking an image of an object such as an organ in the body (abdominal cavity 101).

In the camera 1 of the present embodiment, the control section 5 also controls driving of the motor 8 that rotates the camera unit 19 so that the timing at which the cover lens 14 of the image pickup unit 10 moves to a position where the cover lens 14 matches the opening portion 2b of the camera body 2 is in accordance with the frame rate timing of the image pickup unit 10.

That is, when the camera unit 19 rotates, the control section 5 controls driving of the motor 8 so that the cover lens 14 of the image pickup unit 10 matches the opening portion 2b of the camera body 2 in synchronization with the timing at which the image pickup unit 10 of the camera 1 picks up an object image. As described above, this "timing" is timing at which the center position A of the opening portion 2b of the camera body 2 matches the optical axis O of the object image that impinges on the image pickup unit 10.

As described above, the camera 1 of the present embodiment also has a configuration in which the camera unit 19 is made to rotate, the cover lens 14 of the image pickup unit 10 moves to a position where the cover lens 14 matches the opening portion 2b of the camera body 2 in accordance with the moment (timing) at which the image pickup unit 10 picks up an object image and the cover lens 14 is exposed from the opening portion 2b of the camera body 2. Thus, as in the case of the first embodiment, the duration that the cover lens 14 of the image pickup unit 10 is exposed is shortened, and the camera 1 can thereby prevent blood, mucous membrane or the like from the treated diseased area from scattering over the surface of the cover lens 14 and prevent sticking of contamination such as smoke generated during treatment of the diseased area using a high frequency treatment device.

As described above, the camera 1 of the present embodiment also has a configuration in which the transparent rotating cover 3 rotates and the exposure duration of the cover lens 14 of the image pickup unit 10 that picks up an object image is reduced, that is, the cover lens 14 is exposed only when an object image is picked up, and therefore contamination is less likely to stick to the cover lens 14 and the image pickup unit 10 can always obtain a clear observation image.

Third Embodiment

Figure 11:
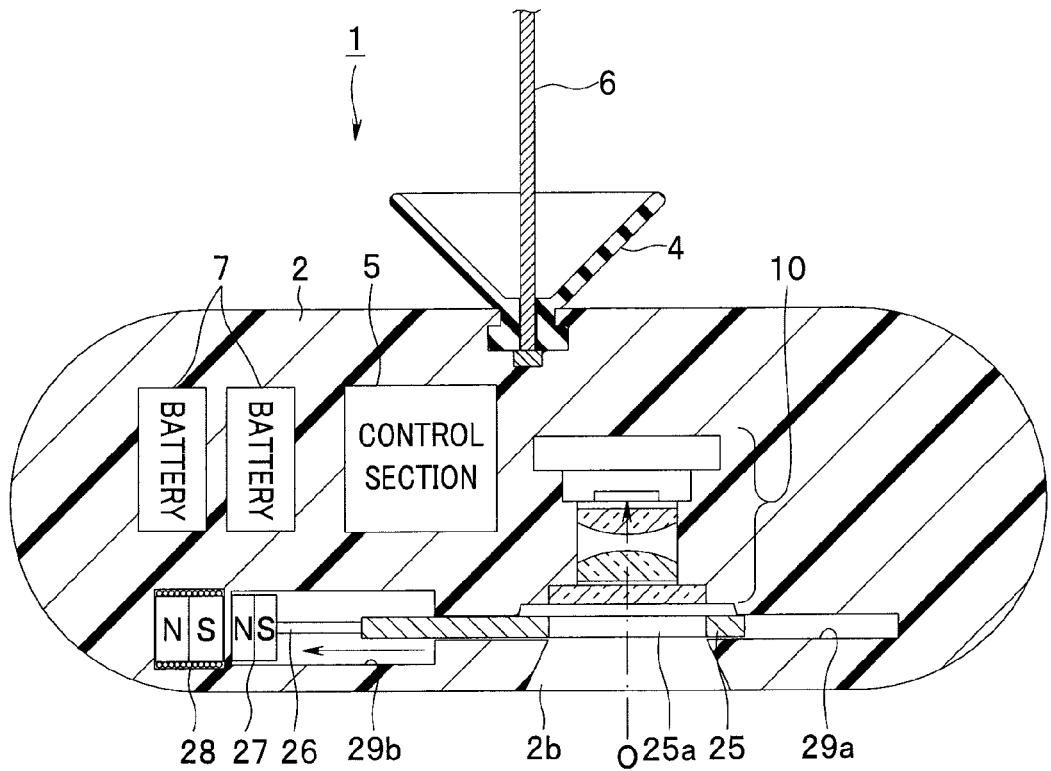
FIG. 11 is a cross-sectional view illustrating a configuration of a camera set up in the abdominal cavity according to a third embodiment of the present invention.
Figure 12:
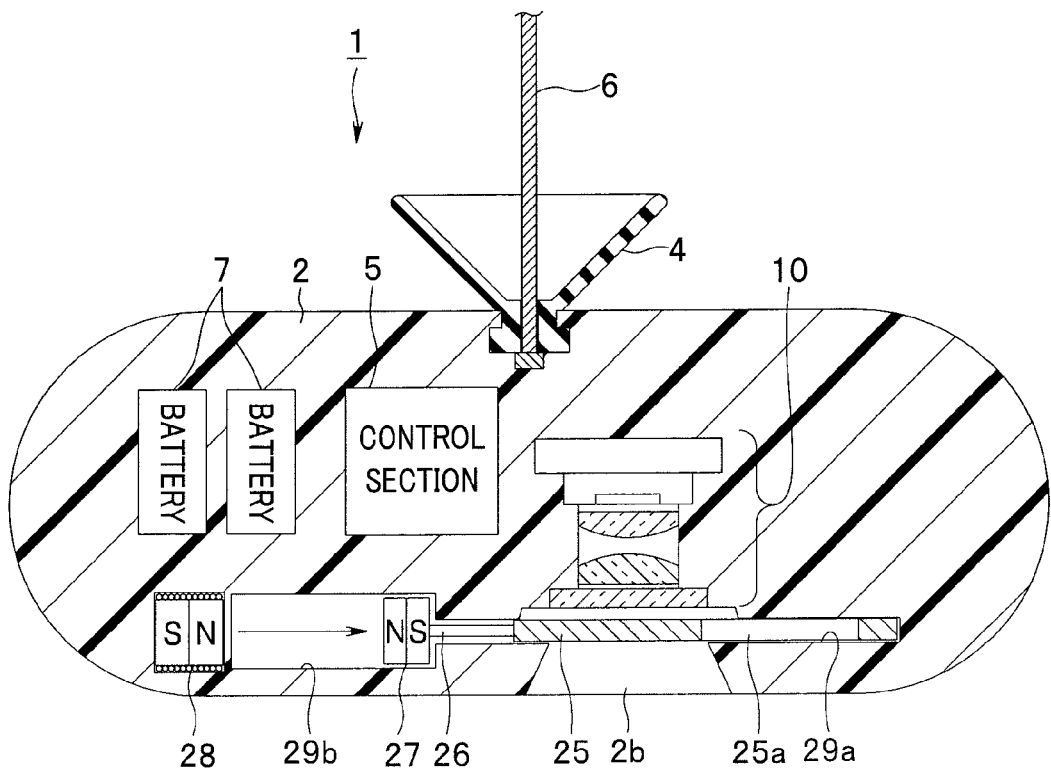
FIG. 12 is a cross-sectional view illustrating the configuration of the camera set up in the abdominal cavity according to the third embodiment when a slide cover has slidingly moved from the state in FIG. 11.

Next, a third embodiment of a camera set up in the abdominal cavity, which is a medical instrument of the present invention, will be described using FIG. 11 and FIG. 12 below. FIG. 11 and FIG. 12 are related to the third embodiment of the present invention, FIG. 11 is a cross-sectional view illustrating a configuration of the camera set up in the abdominal cavity and FIG. 12 is a cross-sectional view illustrating the configuration of the camera set up in the abdominal cavity when a slide cover has slidingly moved from the state in FIG. 11. In the following descriptions, the same components as those in the camera set up in the abdominal cavity of the first embodiment will be assigned the same reference numerals and descriptions of those components and operations/effects will be omitted.

The camera 1 of the present embodiment has a configuration including a slide cover 25, which is tabular covering means (covering section) that covers the cover lens 14 of the image pickup unit 10 instead of the cylindrical rotating cover 3 of the first embodiment.

To be more specific, as shown in FIG. 11 and FIG. 12, the camera 1 is provided with a groove section 29a formed in the camera body 2 so that the tabular slide cover 25 may be slidably disposed. The groove section 29a is formed so as to communicate with the opening portion 2b of the camera body 2 to take in an object image of the image pickup unit 10 and rectilinearly guide the slide cover 25 that slidingly moves leftward or rightward.

One side of the slide cover 25 disposed in the groove section 29a is connected to one end of an axial body 26. Furthermore, a magnet (permanent magnet) 27 is provided at the other end of the axial body 26. The magnet 27 is slidably disposed in a cavity 29b formed so as to communicate with the groove section 29a formed in the camera body 2. Furthermore, an opening portion 25a, which is a circular hole portion, is formed in the slide cover 25. The opening portion 25a also has a hole portion diameter equal to or greater that the diameter of the cover lens 14 so that the entire surface of the cover lens 14 of the image pickup unit 10 may be exposed.

Furthermore, the camera body 2 is provided with an electromagnet 28 at an end of the cavity 29b. The electromagnet 28 is electrically connected to the control section 5 and switching between an S pole and an N pole is controlled by the control section 5.

In the camera 1 of the present embodiment configured as shown above, the switching between the S pole and the N pole of the electromagnet 28 is controlled by the control section 5 based on wireless operation from outside. That is, in the camera 1, the magnet 27 connected to the slide cover 25 via the axial body 26 is given an attractive force or repulsive force by the electromagnet 28 under the control of switching between unlike poles (see FIG. 11) or like poles (see FIG. 12) of the electromagnet 28. The action of the attractive force and repulsive force of the magnetic force causes the slide cover 25 to slidingly move along the groove section 29a. That is, the camera 1 of the present embodiment has a configuration in which the slide cover 25 is slidingly moved along the groove section 29a by the drive section (drive means) through the magnetic action of the magnet 27 and the electromagnet 28.

That is, the camera 1 is configured such that among predetermined positions where the slide cover 25 slides along the groove section 29a by magnetic action of the magnet 27 and the electromagnet 28, the opening portion 25a of the slide cover 25 moves to a position where the opening portion 25a matches the cover lens 14 of the image pickup unit 10 (see FIG. 11).

In the camera 1 of the present embodiment, the electromagnet 28 is also controlled by the control section 5 so that the timing at which the opening portion 25a of the slide cover 25 moves to a position where the opening portion 25a matches the cover lens 14 of the image pickup unit 10 is in accordance with the frame rate timing of the image pickup unit 10.

That is, the control section 5 controls driving of the electromagnet 28 so that the opening portion 25a of the slide cover 25 matches the cover lens 14 of the image pickup unit 10 in synchronization with the timing at which the image pickup unit 10 of the camera 1 picks up an object image when the slide cover 25 slides. This "timing" is timing at which the center on the hole portion axis of the opening portion 25a of the slide cover 25 matches the optical axis O of the object image that impinges on the image pickup unit 10.

As described above, the camera 1 of the present embodiment also has a configuration in which the cover lens 14 of the image pickup unit 10 moves to a position where the cover lens 14 matches the opening portion 25a of the slide cover 25 in accordance with the moment (timing) at which the image pickup unit 10 picks up an object image and the cover lens 14 is exposed from the opening portion 2b of the camera body 2 without the field of view being blocked by the slide cover 25. Thus, in the camera 1, as in the case of the first embodiment, the duration that the cover lens 14 of the image pickup unit 10 is exposed is shortened, and it is thereby possible to prevent blood, mucous membrane or the like from the treated diseased area from scattering over the surface of the cover lens 14 and prevent sticking of contamination by smoke or the like generated when the diseased area is treated using a high frequency treatment device.

As described above, since the camera 1 of the present embodiment also has a configuration in which the slide cover 25 is slidingly moved and the exposure duration of the cover lens 14 of the image pickup unit 10 is shortened, that is, the cover lens 14 is exposed only when an object image is picked up, contamination is less likely to stick to the cover lens 14 and the image pickup unit 10 can always obtain a clear observation image.

Fourth Embodiment

Figure 13:
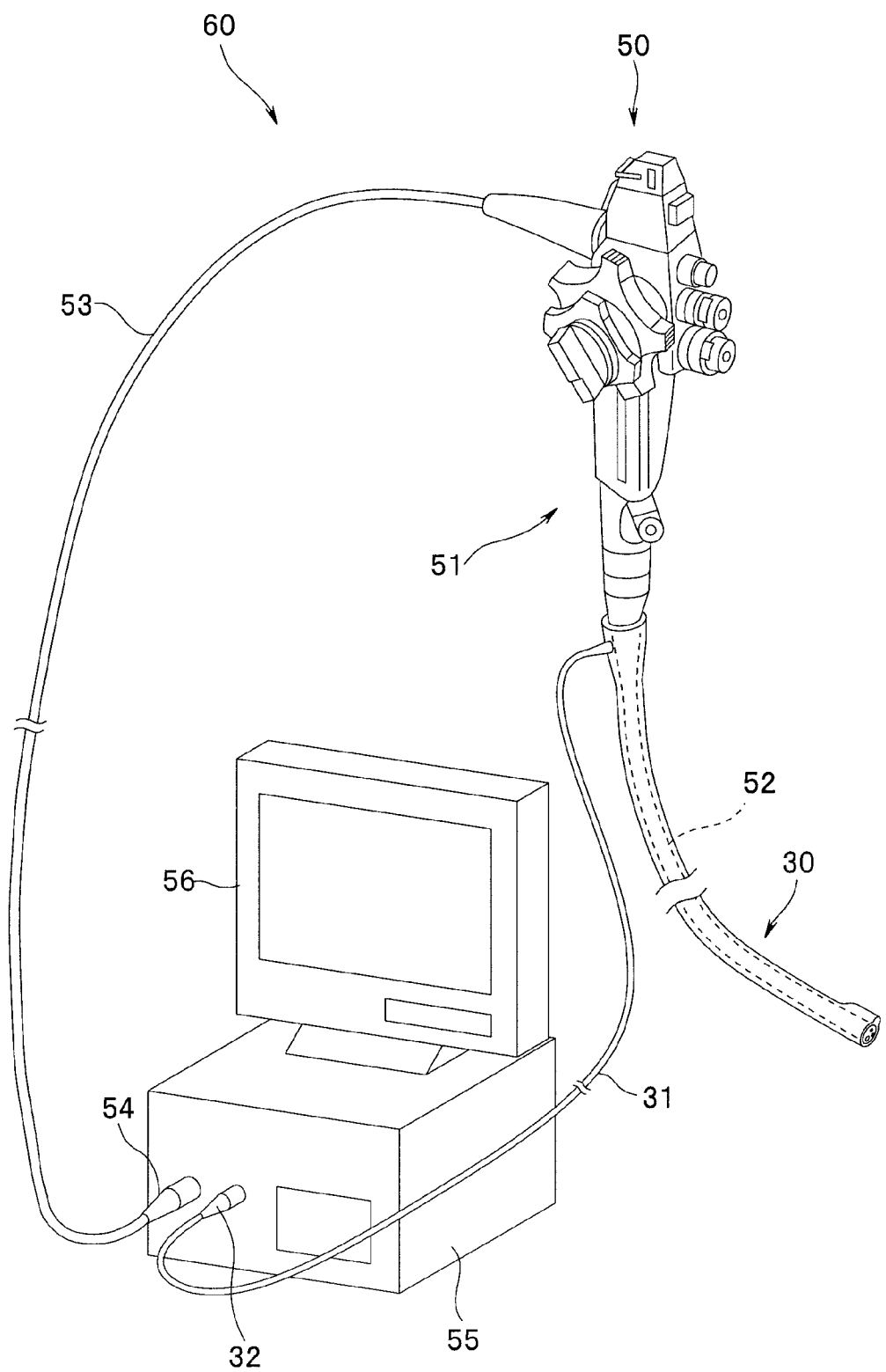
FIG. 13 is a cross-sectional view illustrating a configuration of an endoscope system according to a fourth embodiment of the present invention.
Figure 14:
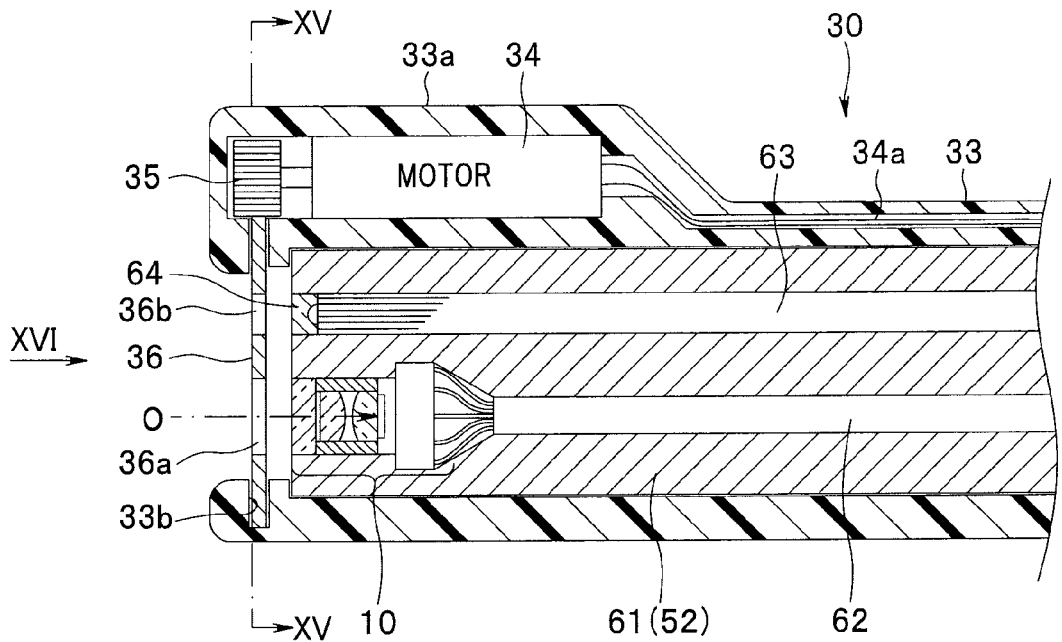
FIG. 14 is a cross-sectional view illustrating the distal end portion of an insertion portion of the endoscope system according to the fourth embodiment.
Figure 15:
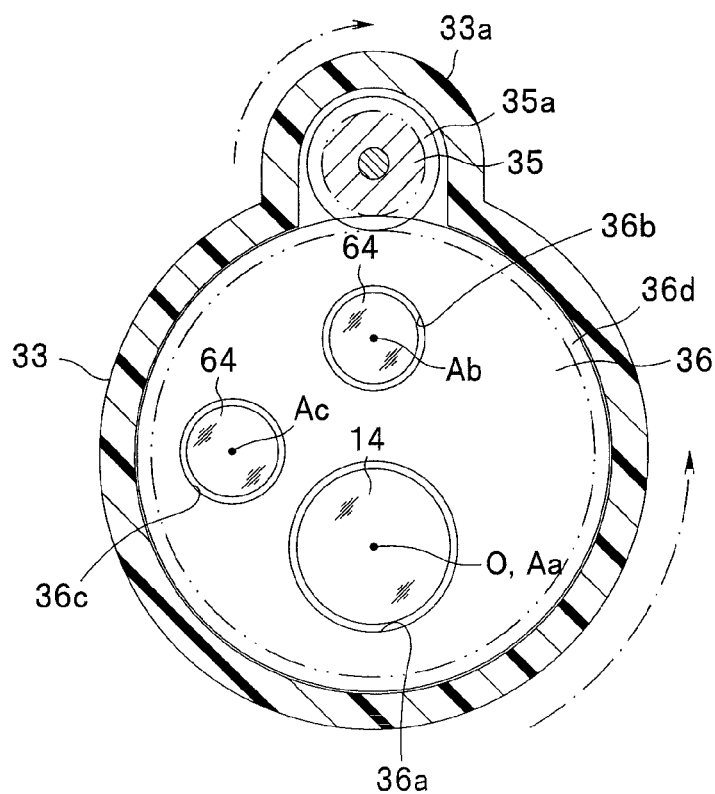
FIG. 15 is a cross-sectional view along XV-XV in FIG. 14 of the endoscope system according to the fourth embodiment.
Figure 16:
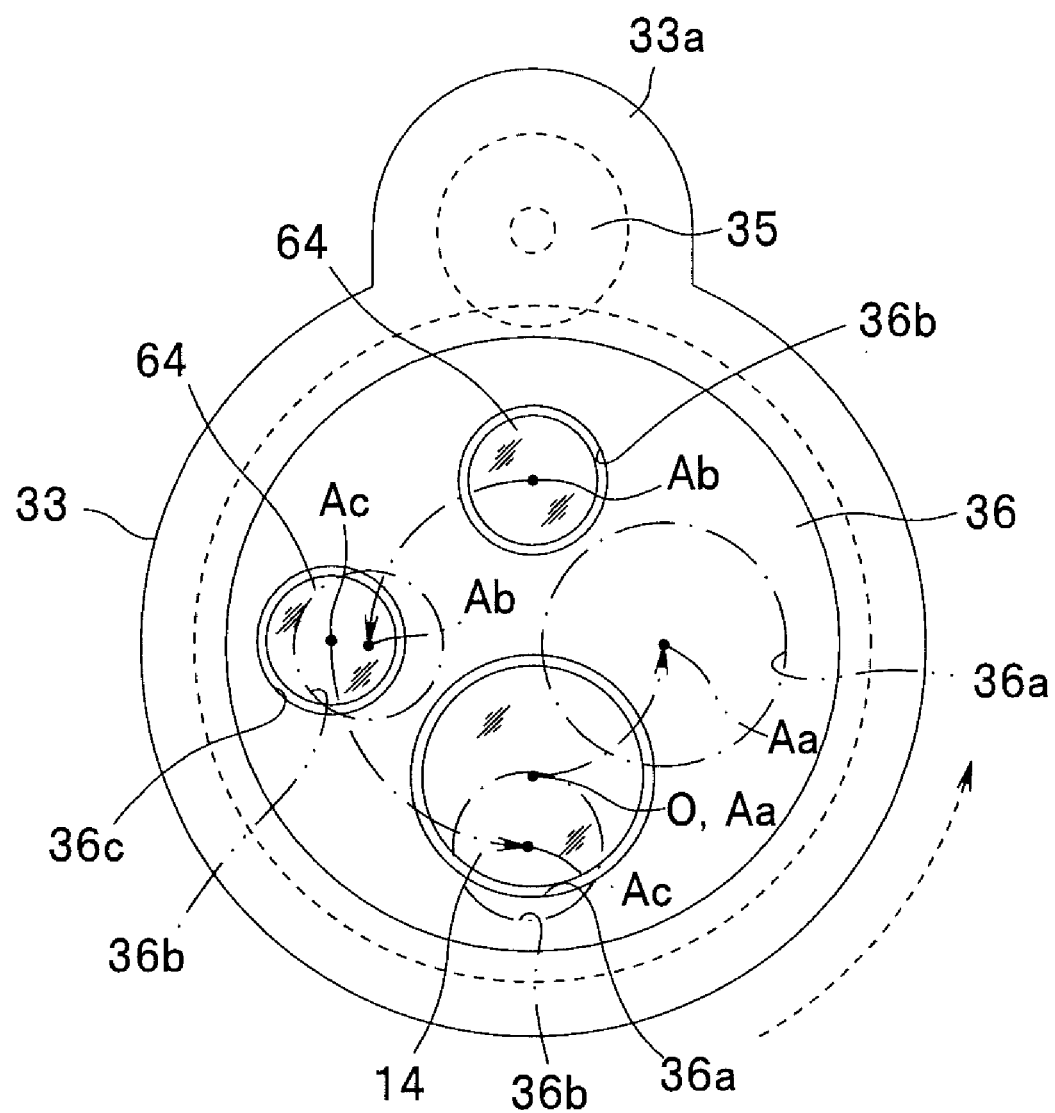
FIG. 16 is a diagram illustrating the endoscope system according to the fourth embodiment viewed from a direction indicated by an arrow XVI in FIG. 14.

Next, a fourth embodiment of a camera set up in the abdominal cavity, which is a medical instrument of the present invention, will be described using FIG. 13 to FIG. 15. FIG. 13 to FIG. 15 are related to the fourth embodiment of the present invention, FIG. 13 is a cross-sectional view illustrating a configuration of an endoscope system, FIG. 14 is a cross-sectional view illustrating the distal end portion of an insertion portion of the endoscope system, FIG. 15 is a cross-sectional view along XV-XV in FIG. 14 and FIG. 16 is a diagram illustrating a view from a direction indicated by an arrow XVI in FIG. 14. In the following descriptions, the same components as those described in the first embodiment will be assigned the same reference numerals and descriptions of those components and operations/effects will be omitted.

As shown in FIG. 13, an endoscope system 60, which is a medical instrument of the present embodiment, is mainly configured by including an endoscope 50, a cover sheath 30, a camera control unit (CCU) 55 which is control means (control section) with a built-in light source device, and a monitor 56 which is drive means (drive source).

The endoscope 50 includes an operation portion 51 and a flexible insertion portion 52 connected to the operation portion. The operation portion 51 is provided with an operation knob for performing bending operation of a bending portion provided in the insertion portion 52 and switches for operating various endoscope functions.

A universal cord 53, which is an electric communication cable, extends from the operation portion 51 and a connector 54 disposed at an end of the universal cord 53 is connected to the CCU 55. Since the endoscope 50 has a conventional configuration, detailed descriptions of the rest of the configuration will be omitted. Furthermore, although the endoscope 50 provided with the flexible insertion portion 52 is described in the present embodiment, a rigid endoscope provided with a rigid insertion portion may also be adopted.

The cover sheath 30 is a soft tubular body into which the insertion portion 52 is inserted, designed to cover the insertion portion 52 of the endoscope 50. A cable 31 extends from a proximal end portion of the cover sheath 30 and a connector 32 disposed at an end of the cable 31 is connected to the CCU 55. When inserted into the cover sheath 30, the insertion portion 52 of the endoscope 50 is fixed by a fixing section (not shown) provided in the cover sheath 30 and the orientation and position thereof are determined.

As shown in FIG. 14 and FIG. 15, the cover sheath 30 has a distal end portion 33a which incorporates a motor 34 at the distal end portion. The motor 34 is connected to an electric wire 34a that passes through the cover sheath 30. The electric wire 34a is disposed in the above described cable 31 that extends from the cover sheath 30 and supplies an electric signal from the CCU 55 to the motor 34. The motor 34 is driven/controlled by the CCU 55.

Furthermore, a rotating cover 36, which is disk-shaped covering means (covering section), is disposed at the distal end portion 33a so as to cover the opening at the distal end of the cover sheath 30. The rotating cover 36 is rotatably disposed along a groove section 33b formed at the distal end portion 33a and a gear groove 36d which is meshed with a gear 35 of the motor 34 is formed in the outer perimeter. Furthermore, three hole portions; opening portions 36a, 36b, and 36c, are formed in the rotating cover 36.

The openings 36a, 36b and 36c are formed so as to expose the cover lens 14, which is an observation window disposed on an end face of a distal end rigid portion 61 provided in the insertion portion 52 of the endoscope 50, and two illumination lenses 64, which are illumination windows, at predetermined rotation positions of the rotating cover 36.

The endoscope 50 of the present embodiment is configured to have a light guide 63 that transmits illumination light from a light source device in the CCU 55 so that illumination light is irradiated onto an object to be examined from the illumination lens 64. Instead of such a configuration, the endoscope may also be configured to have an illumination light source using an LED or the like. The image pickup unit 10 is connected to an image pickup wire 62 disposed in the insertion portion 52.

The endoscope system 60 configured as shown above is configured as shown in FIG. 15 and FIG. 16 such that the rotating cover 36 of the cover sheath 30 is rotated by the motor 34 and the image pickup unit 10 picks up an object image at a position where the three openings 36a, 36b and 36c match the cover lens 14 and the illumination lenses 64 of the image pickup unit 10.

That is, in the endoscope system 60 of the present embodiment, the motor 34 is controlled by the CCU 55 so that the timing at which the rotating cover 36 moves to a position where the cover lens 14 of the image pickup unit 10 matches the opening portion 36a of the rotating cover 36 and the two illumination lenses 64 match the two openings 36b and 36c is also in accordance with the frame rate timing of the image pickup unit 10.

That is, the CCU 55 controls driving of the motor 34 so that when the rotating cover 36 rotates, the opening portion 36a of the rotating cover 36 matches the cover lens 14 of the image pickup unit 10 in synchronization with the timing at which the image pickup unit 10 of the endoscope 50 picks up an object image. This "timing" is timing at which a center position Aa which is the center of the opening on the hole portion axis of the opening portion 36a of the rotating cover 36 matches the optical axis O of the object image that impinges on the image pickup unit 10. Furthermore, in this case, such timing is also timing at which center positions Ab and Ac on the respective hole portion axes of the other two openings 36b and 36c of the rotating cover 36 match the center positions of the two illumination lenses 64.

As described above, the endoscope system 60 of the present embodiment also has a configuration in which the rotating cover 36 moves to a position where the cover lens 14 of the image pickup unit 10 matches the opening portion 36a of the rotating cover 36 in synchronization with the moment (timing) at which the image pickup unit 10 picks up the object image and the cover lens 14 is thereby exposed without the field of view being blocked by the rotating cover 36. In the endoscope system 60 as in the case of the first embodiment, the duration that the cover lens 14 of the image pickup unit 10 is exposed is shortened and it is thereby possible to prevent blood, mucous membrane or the like from the treated diseased area from scattering over the surface of the cover lens 14 and prevent sticking of contamination due to smoke or the like generated when the diseased area is treated using a high frequency treatment device.

As described above, since the endoscope system 60 of the present embodiment is also configured, as in the case of the above described embodiments, to cause the rotating cover 36 to rotate and shorten the exposure duration of the cover lens 14 of the image pickup unit 10 that picks up an object image, contamination is less likely to stick to the cover lens 14 and the image pickup unit 10 can always obtain a clear observation image.

As described above, according to the medical instrument of the aforementioned embodiments, it is possible to prevent deposits from sticking to the observation window of the observation apparatus and obtain a clear observation image.

What is claimed is:

1. A medical instrument that observes an interior of an object to be examined, comprising:
   an image pickup section incorporated in a medical instrument body and provided in the medical instrument body that picks up an image of the object to be examined from an observation window;
   a covering section provided at the medical instrument body so as to cover the observation window and in which an opening portion is formed, the opening portion being capable of exposing the observation window by relative movement of the covering section with respect to the image pickup section;
   a drive section that drives the covering section or the image pickup section; and
   a control section that controls the drive section so as to move the covering section or the image pickup section relatively to each other by synchronizing a timing for the image pickup section to pick up the object image with a timing at which the opening portion and the observation window match in accordance with a frame rate of the image pickup section.

2. The medical instrument according to claim 1, wherein the covering section is rotatably disposed at the medical instrument body.

3. The medical instrument according to claim 1, wherein the covering section is slidably disposed at the medical instrument body.

4. The medical instrument according to claim 1, wherein a center of the opening portion matches an image taking optical axis of the object image at a timing at which the image pickup section picks up the object image.

5. The medical instrument according to claim 4, wherein the covering section is a cylindrical rotating cover driven to rotate by the drive section.

6. The medical instrument according to claim 4, wherein the image pickup section is disposed in the covering section and driven to rotate by the drive section.

7. The medical instrument according to claim 4, wherein the covering section is a tabular body slidingly moved by the drives section.

8. The medical instrument according to claim 7, wherein the drive section is an electromagnet that switches between an attractive force and repulsive force to be given to a magnet provided on the tabular body.

* * * * *